United States Patent
Chevalier et al.

(10) Patent No.: US 6,960,347 B2
(45) Date of Patent: Nov. 1, 2005

(54) COMPOSITION BASED ON N-CHOLESTERYLOXYCARBONYL-4-PARA-AMINOPHENOL AND HYDROQUINONE OR ONE OF ITS DERIVATIVES

(75) Inventors: Veronique Chevalier, Villecresnes (FR); Dang-Man Pham, Sucy-en-Brie (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/784,179

(22) Filed: Feb. 16, 2001

(65) Prior Publication Data

US 2001/0036446 A1 Nov. 1, 2001

(30) Foreign Application Priority Data

Feb. 16, 2000 (FR) ............................................. 00 01915

(51) Int. Cl.⁷ ......................... A61K 7/00; A61K 7/135; A61K 7/021; A61K 7/06
(52) U.S. Cl. ........................ 424/401; 424/63; 424/70.1; 424/62
(58) Field of Search ............................ 424/401, 62, 63, 424/70.1

(56) References Cited

U.S. PATENT DOCUMENTS

| | | | |
|---|---|---|---|
| 5,449,518 A | 9/1995 | Junino et al. | 424/401 |
| 5,523,077 A | 6/1996 | Pawelek et al. | 424/62 |
| 6,159,482 A * | 12/2000 | Tuloup et al. | 424/401 |
| 6,203,781 B1 * | 3/2001 | Chevalier et al. | 424/63 |
| 6,423,854 B1 * | 7/2002 | Philippe et al. | 552/544 |

FOREIGN PATENT DOCUMENTS

| | | |
|---|---|---|
| EP | 0 898 956 A1 | 3/1999 |
| EP | 0 962 224 * | 12/1999 |
| FR | 2 778 561 | 11/1999 |
| GB | 1 349 955 | 4/1974 |
| JP | 61 227516 | 10/1986 |
| JP | 09 077655 | 3/1997 |
| WO | WO 98/07406 | 2/1998 |
| WO | WO 99/10318 | 3/1999 |

OTHER PUBLICATIONS

K. Sakuma et al, *Arch. Pharm. Res.*, vol. 22 (4), pp. 335–339 (1999).

French Search Report issued in French Priority Application No. 0001915 and dated Sep. 19, 2000.

* cited by examiner

*Primary Examiner*—Shengjun Wang
(74) *Attorney, Agent, or Firm*—Oblon, Spivak, McClelland, Maier & Neustadt, P.C.

(57) ABSTRACT

Compositions comprising, in a physiologically acceptable medium, N-cholesteryloxycarbonyl-4-para-aminophenol and hydroquinone or one of its derivatives may be used for depigmenting and/or lightening the skin, the body hair, and/or the head hair by applying such a composition to the skin, the body hair, and/or the head hair.

22 Claims, No Drawings

COMPOSITION BASED ON N-CHOLESTERYLOXYCARBONYL-4-PARA-AMINOPHENOL AND HYDROQUINONE OR ONE OF ITS DERIVATIVES

CROSS REFERENCES TO RELATED APPLICATIONS

This application claims priority to French Patent Application No. 0001915, filed on Feb. 16, 2000, and which is incorporated herein by reference in its entirety.

BACKGROUND OF THE INVENTION

1. Field of the Invention

The present invention relates to cosmetic or dermatologic compositions and to the use of such compositions for depigmenting and/or lightening the skin, body hair and/or head hair. The present invention also relates to methods for the manufacture of compositions useful for depigmenting and/or lightening the skin body hair, and/or head hair.

2. Discussion of the Background

At various times in their life, some people experience the appearance, on the skin and more especially on the hands, of darker and/or more highly colored spots, which confer heterogeneity on the skin. These spots are due to a high concentration of melanin in the keratinocytes situated at the surface of the skin. Indeed, the melanocytes situated in the basal portion of the epidermis produce melanin and deliver this melanin to the surrounding keratinocytes, which then rise to the surface of the epidermis, charged with melanin.

The mechanism for the formation of the pigmentation of the skin, that is to say the formation of melanin, is particularly complex and schematically involves the following main steps:

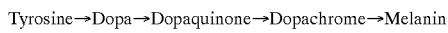

Tyrosine→Dopa→Dopaquinone→Dopachrome→Melanin

Tyrosinase is the main enzyme involved in this sequence of reactions. It catalyzes in particular the reaction for converting tyrosine to Dopa (dihydroxyphenylalanine) and the reaction for converting the Dopa to dopaquinone. This tyrosinase acts only when it is in the state of maturation under the action of certain biological factors.

A substance is recognized as being depigmenting if it acts directly on the vitality of the epidermal melanocytes where melanogenesis occurs and/or if it interferes with one of the steps in the biosynthesis of melanin either by inhibiting one of the enzymes involved in melanogenesis or by being involved as a structural analogue of one of the chemical compounds in the chain for the synthesis of melanin, which chain may then be blocked and thus bring about depigmentation.

The substances most widely used as depigmenting agents are more particularly hydroquinone and its derivatives, in particular its ethers such as hydroquinone monomethyl ether and monoethyl ether. Although they are definitely effective, these compounds are unfortunately not free of side effects because of their toxicity, which can make their use delicate, or even dangerous. This toxicity comes from the fact that they act on the basic mechanisms of melanogenesis by killing cells which then risk disrupting their biological environment and which consequently force the skin to delete them by producing toxins.

Thus, hydroquinone, whose use is in fact legally limited in Europe to a concentration of 2%, is a compound which is particularly irritating and cytotoxic for the melanocyte, whose complete or partial replacement has been envisaged by many authors.

The use of harmless topical depigmenting substances having a high efficacy is most particularly sought for the treatment of regional hyperpigmentations caused by melanocyte hyperactivity, such as idiopathic melasmas, occurring during pregnancy ("mask of pregnancy" or chloasma), or oestroprogestrogen contraception, localized hyperpigmentations caused by benign melanocyte hyperactivity and proliferation, such as senile pigmented spots called actinic lentigo, accidental hyperpigmentations such as photosensitization and post-lesion cicatrization, as well as certain leukodermas such as vitiligo. For the latter hyperpigmentations, short of being able to repigment the damaged skin, depigmentation of the areas of residual normal skin is completed in order to give the whole skin a homogeneous light complexion.

Thus, substances have been sought which are not involved in the mechanism of melanogenesis but which, instead, act upstream on tyrosinase by preventing its activation and are consequently a lot less toxic.

Various depigmenting agents have thus been proposed. In particular, it has been demonstrated that certain aminophenol derivatives have the property of inhibiting melanogenesis even in low concentrations, without demonstrating cytotoxicity. These compounds, which are described in International PCT Patent Application No. WO 99/10318, (U.S. patent application Ser. No. 09/284,490 filed Jun. 21, 1999), comprise in particular N-cholesteryloxycarbonyl-4-para-aminophenol.

SUMMARY OF THE INVENTION

However, a need remains for even more effective compositions.

Accordingly, it is one object of the present invention to provide novel cosmetic or dermatologic compositions.

It is another object of the present invention to provide novel cosmetic or dermatologic compositions which are useful for depigmenting or lightening skin.

It is another object of the present invention to provide novel cosmetic or dermatologic compositions which are useful for depigmenting or lightening human skin.

It is another object of the present invention to provide novel cosmetic or dermatologic compositions which are useful for depigmenting or lightening hair.

It is another object of the present invention to provide novel cosmetic or dermatologic compositions which are useful for depigmenting or lightening human hair.

It is another object of the present invention to provide novel cosmetic or dermatologic compositions which are useful for depigmenting or lightening human head hair.

It is another object of the present invention to provide novel cosmetic or dermatologic compositions which are useful for depigmenting or lightening human body hair.

It is another object of the present invention to provide novel methods for depigmenting or lightening skin.

It is another object of the present invention to provide novel methods for depigmenting or lightening human skin.

It is another object of the present invention to provide novel methods for depigmenting or lightening hair.

It is another object of the present invention to provide novel methods for depigmenting or lightening human hair.

It is another object of the present invention to provide novel methods for depigmenting or lightening human head hair.

It is another object of the present invention to provide novel methods for depigmenting or lightening human body hair.

These and other objects, which will become apparent during the following detailed description have been achieved by the inventors' discovery that when aminophenol derivatives are combined with hydroquinone, these aminophenol derivatives improve hydroquinone's activity and/or make it possible to partially replace hydroquinone while preserving its efficacy.

In particular, it has been discovered that the combination of N-cholesteryloxy-carbonyl-4-para-aminophenol with hydroquinone or one of its derivatives has a depigmenting power greater than that of either of these compounds, considered separately. In other words, this combination potentiates the efficacy of each of these compounds and produces a synergistic effect in the lightening or depigmenting of the skin, of body hair or of head hair.

DETAILED DESCRIPTION OF THE PREFERRED EMBODIMENTS

Thus, in a first embodiment, the present invention provides a composition comprising, in a physiologically acceptable medium, N-cholesterylaxycarbonyl-4-para-aminophenol and hydroquinone or a hydroquinone derivative.

N-cholesterylaxycarbonyl-4-para-aminophenol may be obtained as described in U.S. patent application Ser. No. 09/284,490, filed Jun. 21, 1999, which is incorporated herein by reference.

In the context of the present invention, the term "hydroquinone derivative" is understood to mean optionally substituted hydroquinone monoalkyl ethers and hydroquinone monoaryl ethers. Such hydroquinone ethers are described in Japanese Patent Applications Nos. JP-06 192 062 and JP-61 159 943. It is also understood to means the ethers of hydroquinone and of a heterocyclic alcohol, as described in International PCT Patent Application No. WO 98/07406 (corresponds to U.S. Pat. No. 6,139,854), which is also incorporated herein by reference. The expression "hydroquinone derivative" is further understood to include the (2,5-dihydroxyphenyl) carboxylic acid derivatives described, for example, in application EP-526 302 (corresponds to U.S. Pat. No. 5,449,518), which is also incorporated herein by reference. This term is additionally understood to include hydroquinone which is substituted, in particular, with alkylthio or alkoxy groups.

Examples of preferred hydroquinone derivatives include: 2,5-dihydroxyphenyl propionic acid, the ethyl ester of 2,5-dihydroxyphenyl propionic acid; the lauryl ester of 2,5-dihydroxyphenylpropionic acid; methyl 2,5-dihydroxy-3,4-dimethylphenyl acetate; 2,5-dihydroxy-4-methylphenyl acetic acid; alkyl esters of 2,5-dihydroxy-4-methylphenyl acetic acid; 2,5-dihydroxy-4-methylphenyl propionic acid; ethyl ester of 2,5-dihydroxy-4-phenylpropionic acid; 2,5-dihydroxy-4-methylbenzoic acid; methyl ester of 2,5-dihydroxy-4-methylbenzoic acid; ethyl ester of 2,5-dihydroxy-4-methylbenzoic acid; 2,5-dihydroxy-4-ethylbenzoic acid; 2,5-dihydroxy-4-methoxybenzoic acid; methyl ester of 2,5-dihydroxy-4-methoxybenzoic acid; 2,5-dihydroxy-4-ethoxybenzoic acid; 3-(2,5-dihydroxy-4'-methylphenyl)-1-N-(ω-carboxydecyl) propylamide; 2,5-dihydroxy-4-methylphenylbutanoic acid; 2,5-dihydroxy-4-methylpenylhexanoic acid; 2,5-dihydroxy-4-methoxyphenylacetic acid; methyl ester of 2,5-dihydroxy-4-methoxyphenylacetic acid; 2,5-dihydroxy-4-methoxybenzylamide; methyl 2,5-dihydroxy-3-methoxyphenylacetate 2,5-dihydroxy-3-methoxyphenylpentadecylic acid; methyl ester of 2,5-dihydroxy-3-methoxyphenylpentadecylic acid; 2,5-dihydroxyphenylbutanoic acid; methyl ester of 2,5-dihydroxyphenylbutanoic acid; 2,5-dihydroxyphenylbutylamide 2,5-dihydroxyphenylpentanoic acid; 2,5-di hydroxyphenylhexanoic acid; 2,5-dihydroxyphenyloctanoic acid; 2,5-dihydroxyphenyldecylic acid; methyl ester of 2,5-dihydroxyphenyldecylic acid; 2,5-dihydroxyphenylundecylic acid; methyl ester of 2,5-dihydroxyphenylundecylic acid; 2,5-dihydroxy-3,4-dimethylphenylacetic acid; ethyl-2,5-dihydroxy-4,6-dimethylphenylacetate; 2-(2,5-dihydroxy-4-methoxyphenyl)-N-octylacetamide; 6-(2, 5-dihydroxy-4-methoxyphenyl)hexanoic acid; 4-[(6-methoxyetrahydro-2H-pyran-2-yl)oxyphenol; 4-[(tetrahydro-2H-pyran-2-yl)oxy]phenol; and 4-[(tetrahydro-2H-thiopyran-2-yl)oxy]phenol.

particularly preferred hydroquinone derivatives include:
2,5-dihydroxyphenylpropionic acid;
2,5-dihydroxy-3,4-dimethylphenylacetic acid;
methyl 2,5-dihydroxy-3,4-dimethylphenylacetic acid;
2,5-dihydroxy-4-methylphenylacetic acid;
2,5-dihydroxy-3,4-dimethylphenylpropionic acid;
methyl 2,5-dihydroxy-4-methylphenylacetate;
ethyl 2,5-dihydroxy-4-methylphenylacetate;
propyl 2,5-dihydroxy-4-methylphenylacetate;
isopropyl 2,5-dihydroxy-4-methylphenylacetate;
butyl 2,5-dihydroxy-4-methylphenylacetate;
pentyl 2,5-dihydroxy-4-methylphenylacetate;
isoamyl 2,5-dihydroxy-4-methylphenylacetate; and
2-(2,5-dihydroxy-4-methylphenyl)-N-octylacetamide.

The term "physiologically acceptable medium" is understood to mean a medium suitable for topical application to the skin or its superficial body growths, that is to say which is compatible with the skin, the body hair, the head hair, the nails and the mucous membranes.

The aminophenol derivative and the hydroquinone are present in the composition according to the present invention in a quantity such that they act in synergy to confer on the composition a depigmenting effect which is greater than that obtained with a composition containing only one of these two compounds. For example, the N-cholesteryloxycarbonyl-4-para-aminophenol may be present in a quantity ranging from 0.01 to 5% by weight, and preferably from 0.5 to 2.5% by weight, relative to the total weight of the composition. For its part, the hydroquinone or its derivative may be present in a quantity ranging from 0.1 to 2% by weight, preferably from 0.5 to 1% by weight, relative to the total weight of the composition. In addition to the various other ingredients described below, the balance of the composition may be water.

The composition of the invention may be provided in any galenic form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, it being possible for these spherules to be polymeric nanoparticles such as nanospheres and nanocapsules, or even better lipid vesicles of the ionic and/or nonionic type.

According to a preferred embodiment of the invention, the N-cholesteryloxycarbonyl-4-para-aminophenol may be included in the lamellar phases of ionic or nonionic lipid vesicles, with an oily or aqueous center. These vesicles may be dispersed in an aqueous or oily phase containing hydroquinone or one of its derivatives. As a variant, the hydroquinone or one of its derivatives may be encapsulated into vesicles, which will have an aqueous center in the case of water-soluble derivatives or an oily centre in the case of fat-soluble derivatives.

This composition may be fluid to a greater or lesser degree and may have the appearance of a white or colored cream, an ointment, a milk, a lotion, a serum, a paste or a foam. It may be optionally applied to the skin or to the hair in aerosol form. It may also be provided in solid form, and for example in the form of a stick. It may be used as care product and/or as make-up product for the skin. It may also be in the form of a shampoo or a conditioner.

In a known manner, the composition of the invention may also contain the usual adjuvants in the cosmetic field, such as hydrophilic or lipophilic gelling agents, hydrophilic or lipophilic active agents, preservatives, antioxidants, solvents, perfumes, fillers, sunscreens, pigments, odor absorbers, and coloring matter. The quantities of these various adjuvants are those conventionally used in the field considered, and for example comprise from 0.01 to 20% of the total weight of the composition. These adjuvants, depending on their nature, may be introduced into the fatty phase, into the aqueous phase, into the lipid vesicles and/or into the nanoparticles. In any case, these adjuvants, as well as their proportions, will be chosen so as not to damage the properties sought for the combination of depigmenting agents according to the invention.

When the composition of the invention is an emulsion, the amount of the fatty phase may range from 5 to 80% by weight, and preferably from 5 to 50% by weight, relative to the total weight of the composition. The oils, the emulsifiers and the coemulsifiers used in the composition in the form of an emulsion are chosen from those conventionally used in the field considered. The emulsifier and the coemulsifier are present in the composition in an amount ranging from 0.3 to 30% by weight, and preferably from 0.5 to 20% by weight, relative to the total weight of the composition.

As oils which can be used in the invention, there may be mentioned mineral oils (liquid petroleum jelly), oils of plant origin (avocado oil, soyabean oil), oils of animal origin (lanolin), synthetic oils (perhydrosqualene), silicone oils (cyclomethicone) and fluorinated oils (perfluoropolyethers). It is also possible to use, as fatty substances, fatty alcohols (cetyl alcohol), fatty acids and waxes (carnauba wax, ozokerite).

As emulsifiers and coemulsifiers which can be used in the invention, there may be mentioned for example the esters of fatty acid and polyethylene glycol such as PEG 20 stearate, and the esters of fatty acid and glycerin such as glycerol stearate.

As hydrophilic gelling agents, there may be mentioned in particular carboxyvinyl polymers (carbomer), acrylic copolymers such as acrylate/alkyl acrylate copolymers, polyacrylamides, polysaccharides, natural gums and clays, and, as lipophilic gelling agents, there may be mentioned modified clays such as bentones, metal salts of fatty acids, hydrophobic silica and polyethylenes.

As active agents, there may be used, in particular, polyols, vitamins, keratolytic and/or desquamatory agents, soothing agents and mixtures thereof. Preferably, the composition according to the invention comprises at least one UV-screening agent and/or at least one desquamatory agent. As a variant or in addition, it is also possible to combine N-cholesteryloxycarbonyl-4-para-aminophenol and hydroquinone or one of its derivatives with other depigmenting agents, such as kojic acid and its derivatives, which makes it possible to use the latter in lower doses.

In another embodiment, the present invention provides the use of this composition in a cosmetic preparation for depigmenting and/or lightening the skin, the body hair or the head hair. Thus, the present invention provides a method for depigmenting and/or lightening the skin, the body hair or the head hair, involving applying to the skin, the body hair or the head hair a composition according to the invention.

Although the present method is effective for depigmenting and/or lightening the skin and hair of other mammals, such as dogs, cats, horses, cows, pigs, and chimpanzees, it is preferred that the skin or hair being depigmented and/or lightened be human skin or hair.

The present method of depigmenting and/or lightening of skin, head hair, or body hair may be carried out by applying the present composition to the skin or hair to be depigmented or lightened. Although the exact amount of composition to be applied and the frequency of application will vary with the exact conditions of the skin and hair being treated and the degree of depigmenting and lightening desired, the composition will typically be applied to the skin (or hair) in such an amount so as to achieve a dosage of 0.01 to 4 $mg/cm^2$ of skin, preferably 1 to 2 $mg/cm^2$ of skin, of N-cholesteryloxy-carbonyl-4-para-aminophenol, and a dosage of 0.01 to 8 $mg/cm^2$ of skin, preferably 1 to 4 $mg/cm^2$ of skin, of hydroquinone or derivative thereof. The application of the composition is carried out until the desired level of depigmentation or lightening is achieved, typically for a period ranging from 8 days to 3 months, more typically from 8 days to 4 weeks. Although the present method may be used for depigmenting or lightening even normal skin, in a preferred embodiment, the present method is used for the treatment of regional hyperpigmentations caused by melanocyte hyperactivity, such as idiopathic melasmas, occurring during pregnancy ("mask of pregnancy" or chloasma), or oestroprogestrogen contraception, localized hyperpigmentations caused by benign melanocyte hyperactivity and proliferation, such as senile pigmented spots called actinic lentigo, accidental hyperpigmentations such as photosensitization and post-lesion cicatrization, as well as certain leukodermas such as vitiligo.

In another embodiment, the present invention provides methods for preparing such compositions. Although the exact method used to prepare the present compositions will depend on the type of composition being prepared, the present compositions may be prepared using conventional techniques known to those skilled in the art, with the exception of including the combination of N-cholesteryloxycarbonyl-4-para-aminophenol and hydroquinone or derivative thereof.

other features of the invention will become apparent in the course of the following descriptions of exemplary embodiments which are given for illustration of the invention and are not intended to be limiting thereof.

EXAMPLES

In these examples, the concentrations are expressed in percentage by weight, unless otherwise stated.

Example 1

Test of Depigmentation—Demonstration of the Synergistic Effect

An in vitro biological test (inhibition of the activity of fungal tyrosinase) was used to demonstrate the depigmenting activity of the combination of compounds according to the invention.

This test involves in measuring the absorbance (optical density OD) at 475 nm as a function of time for the hydroquinone dissolved (at various concentrations) in ethanol in the presence of a phosphate buffer, 1 ml of L-tyrosine at $2.0 \times 10^{-3}$ M in a phosphate buffer, 0.1 ml of L-Dopa at $1.0 \times 10^{-4}$ M in a phosphate buffer and 50 µl of a solution of fungal tyrosinase at 1 g/l in a phosphate buffer, compared with a control consisting of ethanol (solvent) used at the same concentration in the phosphate buffer.

The percentage of inhibition is determined by the following equation:

$$\% \text{ inhibition} = \frac{OD_{max,475\,nm}(\text{control}) - OD_{max,475\,nm}(\text{active agent})}{OD_{max,475\,nm}(\text{control})} \times 100$$

The molar concentration of hydroquinone for which an inhibition value of 25% is observed is then determined. A concentration $C_1$ of hydroquinone is thus obtained where $C_1 = 8 \times 10^{-5}$ M.

The N-cholesteryloxycarbonyl-4-para-aminophenol and the hydroquinone are then mixed in the concentrations $C_1$ and $C_2$ where $C_2$ is the concentration of N-cholesteryloxycarbonyl-4-para-aminophenol at its solubility limit in DMSO, that is $C_2 = 6.77 \times 10^{-5}$ M. At the concentration $C_2$, the N-cholesteryloxycarbonyl-4-para-aminophenol exhibits no inhibition of tyrosinase in this test.

The theoretical percentage of inhibition for the mixture (or theoretical IC), corresponding to the sum of the percentages of inhibition observed for the individual compounds, is then calculated and the percentage of inhibition observed (or IC observed) is determined.

The results are the following:

Mixture $C_1 + C_2$:

IC theoretical=24.4%

IC observed=31.8%

Given the accuracy of this test (of the order of 5%), the synergistic effect of the two compounds in combination is thus clearly demonstrated.

Example 2 (Comparative)

Test of Depigmentation

The test described in Example 1 above is used, except that N-ethyloxycarbonyl-4-para-aminophenol was substituted for N-cholesteryloxycarbonyl-4-para-aminophenol.

The results are the following, where $C'_2$ indicates the concentration of N-ethyloxycarbonyl-4-para-aminophenol in order to obtain 25% inhibition of melanogenesis (solvent: ethanol)

$C_1 = 8 \times 10^{-5}$ M $C'_2 = 1.25 \times 10^{-4}$ M

Mixture $C_1 + C'_2$

IC theoretical=49.2%

IC observed=29.4%

It is therefore apparent from this comparative test that no synergistic effect is observed for this combination, even though the aminophenol derivative used has a structure very similar to that of the N-cholesteryloxycarbonyl-4-para-aminophenol tested in Example 1. Without wishing to be bound by this theory, it is probable that the lowest activity of the above combination is the result of a physical and/or chemical interaction between the two molecules tested.

Example 3

Anti-Spot Cream Based on Oleosomes

| Phase A: | |
| --- | --- |
| Sucrose distearate | 2% |
| Oxyethylenated sorbitan stearate containing 4 mols of ethylene oxide | 1.35% |
| Stearic acid | 1% |
| Caprylic/capric triglycerides | 7% |
| Cyclohexasiloxane | 8% |
| Vegetable oils | 7% |
| UV-screening agent | 2% |
| N-cholesteryloxycarbonyl-4-para-aminophenol | 0.5% |

| Phase B: | |
| --- | --- |
| Glycerin | 5% |
| Propylene glycol | 1% |
| Preservative | 1.1% |
| Salicyclic acid | 0.25% |
| Triethanolamine | 0.46% |
| EDTA | 0.05% |
| Demineralized water | qs 100% |

| Phase C: | |
| --- | --- |
| Carbomer | 0.3% |
| Hydroquinone | 2% |
| Demineralized water | 12.6% |

The oily phase A and the aqueous phase B are heated separately to the temperature of 80°. phase B is then poured into phase A, with stirring using a homogenizer, and then the mixture is transferred into a high-pressure homogenizer (500 b, 3 passes). After cooling to room temperature, phase C is added to the oil-in-water emulsion obtained.

This composition may be used for topical application twice daily in order to prevent the appearance of pigmented spots or to attenuate them.

Example 4

Lightening Fluid

The following composition is conventionally prepared.

| N-cholesteryloxycarbonyl-4-para-aminophenol | 0.5% |
| --- | --- |
| Hydroquinone | 1% |
| Salicyclic acid | 0.25% |
| Vegetable oil | 5% |
| Preservatives | 0.65% |
| UV-screening agent | 2% |
| Disodium EDTA | 0.05% |
| Gelling agents | 4.25% |
| Cyclohexasiloxane | 10% |
| Glycerin | 5% |
| Methylglucose sesquistearate | 2% |
| Oxyethylenated (20 EO) cetearyl alcohol and stearyl alcohol | 2% |

-continued

| | |
|---|---|
| Oxyethylenated (60 EO) hydrogenated castor oil | 2.5% |
| Demineralized water | qs 100% |

This fluid may be used for topical application daily, so as to obtain lightening of the skin.

Example 5

Depigmenting Emulsion Free of Surfactant.

| | |
|---|---|
| N-cholesteryloxycarbonyl-4-para-aminophenol | 0.5% |
| Hydroquinone | 0.5% |
| Vegetable oils | 13% |
| Preservatives | 0.3% |
| UV-screening agents | 6% |
| Disodium EDTA | 0.05% |
| Isophthalate/sulphoisophthalate/ dimethylol cyclohexane/diethylene glycol copolymer | 2% |
| Cyclohexasiloxane | 7% |
| Glycerin | 5% |
| Oxyethylenated (60 EO) hydrogenated castor oil | 2.5% |
| Demineralized water | qs 100% |

This emulsion is suitable for lightening sensitive skins.

obviously, numerous modifications and variations of the present invention are possible in light of the above teachings. It is therefore to be understood that, within the scope of the appended claims, the invention may be practiced otherwise than as specifically described herein.

What is claimed is:

1. A composition, comprising, in a physiologically acceptable medium:
   (1) N-cholesteryloxycarbonyl-4-para-aminophenol; and
   (2) hydroquinone.

2. The composition of claim 1, wherein said N-cholesteryloxycarbonyl-4-para-aminophenol is present in an amount of from 0.01 to 5% by weight, relative to the total weight of said composition.

3. The composition of claim 1, wherein said N-cholesteryloxycarbonyl-4-para-aminophenol is present in an amount of from 0.5 to 2.5% by weight, relative to the total weight of said composition.

4. The composition of claim 1, wherein said hydroquinone is present in an amount of 0.1 to 2% by weight, relative to the total weight of said composition.

5. The composition of claim 1, wherein said hydroquinone is present in an amount of 0.5 to 1% by weight, relative to the total weight of said composition.

6. The composition of claim 1, wherein said N-cholesteryloxycarbonyl-4-para-aminophenol is present in an amount of from 0.01 to 5% by weight, relative to the total weight of said composition, and said hydroquinone is present in an amount of 0.1 to 2% by weight, relative to the total weight of said composition.

7. The composition of claim 1, wherein said N-cholesteryloxycarbonyl-4-para-aminophenol is present in an amount of from 0.5 to 2.5% by weight, relative to the total weight of said composition, and said hydroquinone is present in an amount of 0.5 to 1% by weight, relative to the total weight of said composition.

8. The composition of claim 1, wherein said N-cholesteryloxycarbonyl-4-para-aminophenol is included in a lamellar phase of ionic or nonionic lipid vesicles, with an oily or aqueous center.

9. The composition of claim 8, wherein said vesicles are dispersed in an aqueous or oily phase comprising said hydroquinone.

10. The composition of claim 8, wherein said hydroquinone, is encapsulated in said vesicles.

11. The composition of claim 1, further comprising at least one ingredient selected from the group consisting of UV-screening agents and desquamatory agents.

12. A method for depigmenting and/or lightening the skin, body hair, or head hair, comprising applying to the skin, body hair and/or head hair, a composition comprising, in a physiologically acceptable medium:
   (1) N-cholesteryloxycarbonyl-4-para-aminophenol; and
   (2) hydroquinone.

13. The method of claim 12, wherein said N-cholesteryloxycarbonyl-4-para-aminophenol is present in said composition in an amount of from 0.01 to 5% by weight, relative to the total weight of said composition.

14. The method of claim 12, wherein said N-cholesteryloxycarbonyl-4-para-aminophenol is present in said composition in an amount of from 0.5 to 2.5% by weight, relative to the total weight of said composition.

15. The method of claim 12, wherein said hydroquinone is present in said composition in an amount of 0.1 to 2% by weight, relative to the total weight of said composition.

16. The method of claim 12, wherein said hydroquinone is present in said composition in an amount of 0.5 to 1% by weight, relative to the total eight of said composition.

17. The method of claim 12, wherein said N-cholesteryloxycarbonyl-4-para-aminophenol is present in said composition in an amount of from 0.01 to 5% by weight, relative to the total weight of said composition, and said hydroquinone is present in said composition in an amount of 0.1 to 2% by weight, relative to the total weight of said composition.

18. The method of claim 12, wherein said N-cholesteryloxycarbonyl-4-para-aminophenol is present in said composition in an amount of from 0.5 to 2.5% by weight, relative to the total weight of said composition, and said hydroquinone is present in said composition in an amount of 0.5 to 1% by weight, relative to the total weight of said composition.

19. The method of claim 12, wherein said N-cholesteryloxycarbonyl-4-para-aminophenol is included in a lamellar phase of ionic or nonionic lipid vesicles, with an oily or aqueous center.

20. The method of claim 19, wherein said vesicles are dispersed in an aqueous or oily phase containing hydroquinone.

21. The method of claim 19, wherein said hydroquinone is encapsulated in said vesicles.

22. The method of claim 12, wherein said composition further comprises at least one ingredient selected from the group consisting of UV-screening agents and desquamatory agents.

* * * * *

UNITED STATES PATENT AND TRADEMARK OFFICE
CERTIFICATE OF CORRECTION

PATENT NO. : 6,960,347 B2 Page 1 of 1
DATED : November 1, 2005
INVENTOR(S) : Veronique Chevalier et al.

It is certified that error appears in the above-identified patent and that said Letters Patent is hereby corrected as shown below:

Column 10,
Lines 37 and 39, delete "in said composition".

Signed and Sealed this

Fourteenth Day of February, 2006

JON W. DUDAS
*Director of the United States Patent and Trademark Office*